(12) United States Patent
Laitinen

(10) Patent No.: US 7,910,737 B2
(45) Date of Patent: Mar. 22, 2011

(54) PROCESS FOR THE MANUFACTURING OF 7-ETHYL-10-HYDROXY CAMPTOTHECIN

(75) Inventor: Ilpo Laitinen, Espoo (FI)

(73) Assignee: Fermion Oy, Espoo (FI)

( * ) Notice: Subject to any disclaimer, the term of this patent is extended or adjusted under 35 U.S.C. 154(b) by 830 days.

(21) Appl. No.: 11/883,576

(22) PCT Filed: Feb. 6, 2006

(86) PCT No.: PCT/FI2006/000034
§ 371 (c)(1),
(2), (4) Date: Sep. 18, 2007

(87) PCT Pub. No.: WO2006/082279
PCT Pub. Date: Aug. 10, 2006

(65) Prior Publication Data
US 2008/0103309 A1    May 1, 2008

Related U.S. Application Data

(60) Provisional application No. 60/650,175, filed on Feb. 7, 2005.

(51) Int. Cl.
*C07D 491/22* (2006.01)
*C07D 491/12* (2006.01)

(52) U.S. Cl. .................................... 546/48; 546/89

(58) Field of Classification Search .............. 546/48, 546/89
See application file for complete search history.

(56) References Cited

U.S. PATENT DOCUMENTS

| | | | |
|---|---|---|---|
| 4,473,692 | A | 9/1984 | Miyasaka et al. |
| 4,604,463 | A | 8/1986 | Miyasaka et al. |
| 4,894,456 | A | 1/1990 | Wall et al. |
| 5,053,512 | A | 10/1991 | Wani et al. |
| 6,121,451 | A | 9/2000 | Henegar et al. |
| 6,444,820 | B1 | 9/2002 | Henegar et al. |
| 6,476,043 | B1 | 11/2002 | Toutain et al. |
| 6,723,729 | B2 | 4/2004 | Henegar |
| 2004/0106830 | A1 | 6/2004 | Ogawa et al. |
| 2008/0103309 | A1 | 5/2008 | Laitinen |
| 2008/0182990 | A1 | 7/2008 | Vishnukant et al. |

FOREIGN PATENT DOCUMENTS

| | | |
|---|---|---|
| EP | 1 378 505 A1 | 1/2004 |
| WO | WO-96/31513 A1 | 10/1996 |
| WO | WO-02/066416 A1 | 8/2002 |
| WO | WO-03/074527 A1 | 9/2003 |
| WO | WO-03/089413 A1 | 10/2003 |
| WO | WO-2005/117879 A1 | 12/2005 |

OTHER PUBLICATIONS

Henegar et al., "Practical Asymmetric Synthesis of (S)-4-Ethyl-7,8-dihydro-4-hydroxy-1H-pyrano[3,4-f]indolizine-3,6,10(4H)-trione, a Key Intermediate for the Synthesis of Irinotecan and Other Camptothecin Analogs," J. Org. Chem., American Chemical Society, vol. 62, 1997, pp. 6588-6597, XP-002322583, ISSN: 0022-3263.
Sawada et al., "Synthesis and Antitumor Activity of 20(S)-Camptothecin Derivatives: Carbamate-Linked, Water-Soluble Derivatives of 7-Ethyl-10-hydroxycamptothecin[1]," Chemical and Pharmaceutical Bulletin, Pharmaceutical Society of Japan, vol. 39, No. 6, 1991, pp. 1446-1454, XP000653715, ISSN: 0009-2363.
Shutske et al., "A novel synthesis of the isoxazolo[5,4,3-kl]acriding ring system," J. Heterocyclic Chem., vol. 27, No. 6, 1990, pp. 1617-1621, XP002386600.
Third Party Observations Under Article 115 EPC—EP Application No. 06 708 891.4 (EP 1 846 371) (May 16, 2009).
Third Party Observations Pursuant to Article 115 EPC—EP Application No. 06 708 891.4 (EP 1 846 371) (Apr. 17, 2009).

*Primary Examiner* — Charanjit S Aulakh
(74) *Attorney, Agent, or Firm* — Birch, Stewart, Kolasch & Birch, LLP

(57) ABSTRACT

The invention discloses the preparation method of 7-ethyl-10-hydroxycamptothecin from 4-ethyl-7,8-dihydro-4-hydroxy-1H-pyrano[3,4-f]indolizine-3,6,10(4H)-trione and 1-(2-amino-5-hydroxyphenyl)-propan-1-one using higher reaction temperature and faster heating to that temperature.

10 Claims, No Drawings

PROCESS FOR THE MANUFACTURING OF 7-ETHYL-10-HYDROXY CAMPTOTHECIN

This application is the National Phase of PCT/FI2006/000034 filed on Feb. 6, 2006, which claims priority under 35 U.S.C. §119(e) on U.S. Provisional Application No(s). 60/650,175 filed on Feb. 7, 2005, the entire contents of which are hereby incorporated by reference.

FIELD OF THE INVENTION

This invention relates to a process for the manufacturing of 7-ethyl-10-hydroxy camptothecin, which is an important intermediate in the preparation of camptothecin derivatives, specially irinotecan, used as pharmaceuticals.

BACKGROUND OF THE INVENTION

Irinotecan hydrochloride, (S)-4,11-diethyl-3,4,12,14-tetrahydro-4-hydroxy-3,14-dioxo-1H-pyrano[3',4':6,7]-indolizino[1,2-b]quinolin-9-yl [1,4'-bipiperidine]-1'-carboxylate hydrochloride or 7-ethyl-10-[4-(1-piperidino)-1-piperidino]carbonyloxycamptothecin hydrochloride, having the formula I

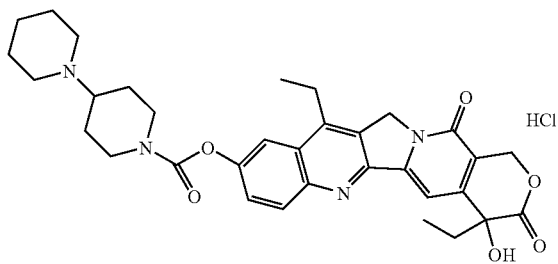

I is a camptothecin analog and topoisomerase I inhibitor. Its trihydrate form has been approved in 1996 in the United States for the treatment of colon cancer, but it is also of interest for treatment of other cancers, such as cancers of the lung, the stomach and the pancreas.

Irinotecan is usually prepared semisynthetically from natural camptothecin, which is extracted from a Chinese tree, *Camptotheca acunzinata*. U.S. Pat. No. 4,604,463 describes several camptothecin derivatives, including irinotecan, its pharmaceutically acceptable salts and preparation thereof starting from natural camptothecin. U.S. Pat. No. 6,121,451 discloses intermediates and process for the synthesis of camptothecin derivatives, e.g. irinotecan hydrochloride, including synthetic route to starting material, 7-ethyl-10-hydroxy camptothecin.

Sawada et al., Chem. Pharm. Bull. 39(6), 1446-1454 (1991), describes the preparation of irinotecan hydrochloride trihydrate from natural camptothecin in five steps and about 20% of overall yield.

Natural camptothecin contains impurities, which are difficult to remove. The purification by chromatographic methods is mentioned e.g. in U.S. Pat. No. 4,473,692, where 7-ethyl-10-hydroxycamptothecin is made from 7-ethylcamptothecin-1-oxide. The availability of natural camptothecin may also limit the production of irinotecan.

Synthetically can be obtained a product, where there are less impurities and they are easier to remove. In U.S. Pat. No. 6,121,451 there has been presented a synthetic route to 7-ethyl-10-hydroxy camptothecin. The obtained product has been used without purification for the preparation of irinotecan. Crude irinotecan so produced is purified by a chromatographic method, which is not applicable in industrial scale. WO 02/066416 describes the method for the preparation of 7-ethyl-10-hydroxy camptothecin by a reaction of 4-ethyl-7,8-dihydro-4-hydroxy-1H-pyrano[3,4-f]indolizine-3,6,10(4H)-trione and 1-(2-amino-5-hydroxyphenyl)-propan-1-one in toluene:AcOH, 1:1, whereafter the reaction mixture is condensed, toluene is added, and the mixture is condensed again. The residue is slurried in acetone, filtered and washed with acetone. The product was achieved as black solid. Yield was 89%, purity 97.7%. Wall et al. have described in general terms the preparation of racemic 7-ethyl-10-hydroxycamptothecin in U.S. Pat. No. 4,894,456 and enantiomerically enriched forms in U.S. Pat. No. 5,053,512, but no examples for the preparation of 7-ethyl-10-hydroxycamptothecin are given.

For the reasons above there exists a need to produce 7-ethyl-10-hydroxycamptothecin synthetically by industrially applicable method to ensure the availability of high quality raw material for the preparation of irinotecan.

Now the inventor has noticed that pure 7-ethyl-10-hydroxy camptothecin can be achieved in high yield, if higher reaction temperatures and faster heating to that temperature are used. The product can be isolated by crystallization, and pure product is achieved without recrystallization or other purification methods. Also, highly pure irinotecan using 7-ethyl-10-hydroxycamptothecin of the invention as a starting material can be obtained without specific purification methods.

DETAILED DESCRIPTION OF THE INVENTION

The present invention is directed to a preparation method of 7-ethyl-10-hydroxycamptothecin from 4-ethyl-7,8-dihydro-4-hydroxy-1H-pyrano[3,4-f]indolizine-3,6,10(4H)-trione (irino-trione) and 1-(2-amino-5-hydroxyphenyl)-propan-1-one (AHPP). It has been noticed that if the reaction temperature is above 100° C. and the heating to the reaction temperature is done rapidly, the product achieved is easy to crystallize directly from the reaction mixture and no distillation to dryness or recrystallization or additional purification e.g. by chromatographic methods as used in prior art are needed to achieve the product in high yield and purity.

Rapid heating means that the temperature is raised to reaction temperature in less than about 45 minutes even in industrial scale, which in this case may be some kilos product with the reaction volume of about 40 to 100 liters.

Another aspect of the present invention is the preparation of irinotecan using 7-ethyl-10-hydroxycamptothecin made by the method of the present invention as a starting material.

Natural camptothecin is known to have the S-configuration at the 20-position. Synthetic derivatives can be made as racemic compounds or as enantiomerically pure substances, which, as well as pharmaceutically acceptable salts thereof, are included in the invention. Resolution can be made after the synthesis, or desired enantiomers can be used as starting compounds.

7-ethyl-10-hydroxycamptothecin is prepared by a reaction of 4-ethyl-7,8-dihydro-4-hydroxy-1H-pyrano[3,4-f]indolizine-3,6,10(4H)-trione (irino-trione) and 1-(2-amino-5-hydroxyphenyl)-propan-1-one (AHPP) in a suitable solvent, which can be a mixture of aromatic or aliphatic hydrocarbon with an organic acid, e.g. toluene and acetic acid or xylene and acetic acid can be used. The ratio of the hydrocarbon to the acid is not important, but both are needed in the reaction.

A suitable acid catalyst is also needed. Sulphonic acids, e.g. p-toluenesulfonic acid can be used.

Irino-trione can be made e.g. as described in U.S. Pat. No. 4,981,968 or U.S. Pat. No. 5,053,512 and AHPP can be made e.g. as described in WO 02/066416, which are all incorporated herein as reference.

The reaction mixture is heated to the reaction temperature which is above 100° C. in less than about 45 minutes, and kept there for a sufficient time for the reaction to complete. In one embodiment of the invention reflux temperature of about 103° C.-105° C. is used as a reaction temperature. The reaction time may be about 5 to 8 hours. Preferably the temperature is raised to reaction temperature in 10 to 30 minutes, most preferably in 10 to 20 minutes. The time depends on the amount of the reagents, but even in pilot and industrial scale it should be no longer than about 45 minutes.

During the reaction, after about two hours part of the water formed in the reaction is distilled off as an azeotrophe with the reaction solvents. 7-ethyl-10-hydroxy camptothecin obtained in this reaction will be either anhydrous or hydrated, depending on the amount of the water removed in this distillation. After the reaction has been completed, a suitable crystallization solvent is added, and the mixture is boiled to dissolve all or at least part of the product and cooled to effect crystallization. Suitable crystallization solvents are aliphatic alcohols, organic acids and nitrites, e.g. acetic acid, butanol, ethanol, methanol, 2-propanol, or acetonitrile, can be used. Preferably 1-butanol or ethanol is used as a crystallization solvent. No additional purification steps like chromatographic purification, as used in prior art, are needed. The crystallized product is isolated by a suitable method known in the art, e.g. by centrifuging or filtration. The purity of the product as measured by High Performance Liquid Chromatography (HPLC, as the area % of the main peak) is at least 99.8%.

The reaction temperature and the time in which the temperature is achieved, are critical to the purity of the product. If temperatures 100° C. or below and/or longer times to reach the temperature are used, more impurities are produced. Using higher temperatures and faster heating improves also the yield significantly. Faster heating is used in pilot and industrial scale, which in the production of irinotecan and its starting materials, as also 7-ethyl-10-hydroxycamptothecin is, may be small, starting even from tens or hundreds of grams of reagents and about 1000 milliliters of solvent. Typical production scale is some kilograms of the product and reaction volume of some tens of liters, e.g. about 40 to 100 liters.

7-ethyl-10-hydroxy camptothecin made by the method of the invention may be used in the preparation of high purity irinotecan by its reaction with 1,4'-bipiperidinyl-1'-carbonyl chloride e.g. as described in U.S. Pat. No. 6,121,451.

The invention will be further clarified by the following nonlimiting examples which are intended to be purely exemplary to the invention.

EXAMPLES

Example 1

7-ethyl-10-hydroxy camptothecin hydrate 100 g of (4S)-4-Ethyl-7,8-dihydro-4-hydroxy-1H-pyrano[3,4-f]indolizine-3,6,10(4H)-trione, 68 g of 1-(2-amino-5-hydroxyphenyl)propan-1-one, 7.2 g of p-toluene sulfonic acid, 800 ml of toluene and 600 ml of acetic acid were charged. The mixture was heated to reflux (about 103° C.) in about 20 minutes and refluxed for 2 hours whereafter 300 ml was distilled off. The mixture was refluxed for an additional 3 hours. 1-Butanol (2400 ml) was added at 80-90° C. The mixture was refluxed for 10-15 minutes. The mixture was cooled to room temperature and stirred for about 20 hours. The crystalline product was filtered and washed with 1-butanol (100 ml) and ethanol (600 ml).

The slightly yellowish product was dried under reduced pressure at 60-70° C.

The yield was 141 g (90.5%).

The HPLC-purity was 99.9%.

Example 2

7-ethyl-10-hydroxy camptothecin hydrate 25 g of (4S)-4-Ethyl-7,8-dihydro-4-hydroxy-1H-pyrano[3,4-f]indolizine-3,6,10(4H)-trione, 17 g of 1-(2-amino-5-hydroxyphenyl)propan-1-one, 2.5 g of p-toluene sulfonic acid, 150 ml of toluene and 200 ml of acetic acid were charged. The mixture was heated to reflux (about 103° C.) in 15 minutes. The mixture was refluxed for 2 hours and then 50 ml was distilled off. The mixture was refluxed for an additional 3 hours. Ethanol (400 ml) was added at 60-70° C. The mixture was refluxed for 10-15 minutes. The mixture was cooled to room temperature and stirred for about 20 hours. The mixture was cooled to 0±5° C. and stirred for about 2 hours.

The crystalline product was filtered and washed with ethanol (15 ml).

The product was dried under reduced pressure at 40-50° C.

The yield was 35.5 g (91.0%).

The HPLC-purity was 99.9%.

Example 3

Irinotecan Hydrochloride

7-Ethyl-10-hydroxycamptothecin*H$_2$O (10 g) and pyridine (120 ml) were charged. A solution of [1,4']bipiperidinyl-1'-carbonyl chloride hydrochloride (9.6 g, 1.4 ekv) and triethylamine (8.5 ml, 2.5 ekv) in methylene chloride (150 ml) was added. The mixture was stirred for 2 hours at room temperature. The mixture was distilled to dryness under reduced pressure. Water (150 ml) was added and the pH was adjusted to 4.0 by hydrochloric acid (5%) at about 80° C. The mixture was cooled to 0-5° C. and stirred for about 20 hours. The crystalline compound was filtered and washed with water. The product was dried under reduced pressure. The yield was 13.2 g (80%).

Example 4

Irinotecan Hydrochloride

7-Ethyl-10-hydroxycamptothecin (4.5 g) and pyridine (60 ml) were charged in a reaction vessel. A solution of [1,4']-bipiperidinyl-1'-carbonyl chloride hydrochloride (3.44 g) and triethylamine (4.8 ml) in 75 ml of methylene chloride was added at 30-40° C. The mixture was stirred for 1.5 hours at 30-40° C. 4-piperidinopiperidine (0.58 g) was added and the mixture was stirred for 0.5 hour. Methylene chloride and pyridine were distilled off until the volume of the residue was about 25 ml. Acetonitrile (100 ml) was added and the mixture was heated to about 60° C. The mixture was cooled to room temperature and 15 ml of 5% aqueous hydrochloric acid was added. The mixture was stirred about 20 hours at room temperature. The mixture was cooled to 0±5. The crystalline compound was filtered and washed with acetonitrile:water 10:1 mixture (10 ml) and acetonitrile (10 ml). The product was dried under reduced pressure. The yield was 6.4 g (90%).

The invention claimed is:

1. A process for the preparation of 7-ethyl-10-hydroxy-camptothecin comprising the steps:
   a) charging a reaction vessel with a reaction mixture comprising (4S)-4-ethyl-7,8-dihydro-4-hydroxy-1H-pyrano[3,4-f]indolizine-3,6,10(4H)-trione, 1-(2-amino-5-hydroxyphenyl)-propan-1-one, a catalyst and a reaction solvent,
   b) heating the reaction mixture to a reaction temperature greater than 100° C., wherein said heating is accomplished in less than 45 minutes,
   c) allowing the reaction to complete in said reaction mixture,
   d) adding a crystallization solvent to said reaction mixture to crystallize said 7-ethyl-10-hydroxy-camptothecin, and
   e) isolating the crystalline product from said reaction mixture which has said crystallization solvent added thereto.

2. The process of claim 1 wherein heating the reaction mixture in step b) is accomplished in 10 to 30 minutes.

3. The process of claim 1 wherein heating the reaction mixture in step b) is accomplished in 10 to 20 minutes.

4. The process of claim 1 which is done at production scale.

5. The process of claim 1 wherein the reaction temperature is the reflux temperature of the reaction mixture.

6. The process of claim 1 further comprising:
   distilling off part or all of the water formed in the reaction.

7. The process of claim 1, wherein the 7-ethyl-10-hydroxy camptothecin that is prepared has a purity as measured by High Performance Liquid Chromatography (HPLC) of greater than or equal to 99.8%.

8. The process according to claim 1 further comprising the step of reacting 7-ethyl-10-hydroxy camptothecin with [1,4']bipiperidinyl-1'-carbonyl chloride to produce irinotecan.

9. The process of claim 1, wherein the volume of the reaction solvent is at least 1000 mL.

10. The process of claim 1, wherein the crystallization solvent in step d) is ethanol or 1-butanol.

* * * * *